United States Patent [19]

Pileski et al.

[11] Patent Number: 5,500,918
[45] Date of Patent: Mar. 19, 1996

[54] BIFURCATED FIBER BUNDLE IN SINGLE HEAD LIGHT CABLE FOR USE WITH MULTI-SOURCE LIGHT BOX

[75] Inventors: Michael J. Pileski, Skaneateles; Robert J. Wood, Syracuse; Connie R. Walts, Auburn, all of N.Y.

[73] Assignee: Welch Allyn, Inc., Skaneatles Falls, N.Y.

[21] Appl. No.: 364,951

[22] Filed: Dec. 28, 1994

[51] Int. Cl.⁶ .............................. G02B 6/06; A61B 1/00
[52] U.S. Cl. .............................. 385/117; 385/89; 606/16; 600/101; 600/160
[58] Field of Search ................................. 385/115, 116, 385/118, 117, 121, 72, 76, 78, 88, 89, 119; 362/32; 315/136; 128/4, 6, 7, 8; 606/2, 16–18

[56] References Cited

U.S. PATENT DOCUMENTS

| | | | |
|---|---|---|---|
| 3,638,013 | 1/1972 | Keller | 362/32 |
| 3,775,606 | 11/1973 | Bazell et al. | 362/32 |
| 3,933,409 | 1/1976 | Kloots | 385/115 X |
| 4,048,486 | 9/1977 | Kriege | 362/32 |
| 4,325,606 | 4/1982 | Ikuno et al. | 385/117 X |
| 4,579,410 | 4/1986 | Scrivo | 385/115 X |
| 4,589,404 | 5/1986 | Barath et al. | 385/117 X |
| 4,881,810 | 11/1989 | Hasegawa | 385/117 |
| 5,000,535 | 3/1991 | Churchill | 385/115 |
| 5,061,995 | 10/1991 | Lia et al. | 385/117 X |
| 5,066,122 | 11/1991 | Krauter | 385/117 |
| 5,083,059 | 1/1992 | Graham et al. | 313/631 |
| 5,144,190 | 9/1992 | Thomas et al. | 313/113 |
| 5,144,201 | 9/1992 | Graham et al. | 313/634 |
| 5,291,100 | 3/1994 | Wood | 315/136 |
| 5,337,735 | 8/1994 | Salerno | 385/117 |
| 5,402,508 | 3/1995 | O'Rourke et al. | 385/31 |

Primary Examiner—Rodney B. Bovernick
Assistant Examiner—Hemang Sanghavi
Attorney, Agent, or Firm—Harris Beach & Wilcox

[57] ABSTRACT

A light cable for transmitting light from a light source to the distal end of an imaging tool requiring a beam of directed light. The light cable is provided with a flexible outer cable member including at least one layer of protective material, a bundle of optic fibers contained within said flexible outer cable member, a first adaptor for connecting one end of the light cable to an imaging tool, and a second adaptor for connecting the other end of the light cable to a light box. The second adaptor is formed to split the bundle of optic fibers into at least two end segments. The light cable is employed in conjunction with a light box having two lamps so that when one burns out, the other may be quickly activated to continue illumination at the distal end of the tool. Alternatively, both lamps may be operated simultaniously to increase illunimation.

17 Claims, 3 Drawing Sheets

BIFURCATED FIBER BUNDLE IN SINGLE HEAD LIGHT CABLE FOR USE WITH MULTI-SOURCE LIGHT BOX

BACKGROUND OF THE INVENTION

1. Field of the Invention

This invention relates in general to illumination systems for tools requiring a beam of directed light to illuminate a working area or target object and, in particular, to a fiber optic cable connectable between such a tool and a light box. More specifically, but without restriction to the particular embodiment hereinafter described in accordance with the best mode of practice, this invention relates to a bifurcated single head light bundle for use with a light box having a pair of lamps capable of being illuminated consecutively to provide extended operating time for the tool.

2. Discussion of the Related Art

There has previously been proposed a number of imaging tools for probing into generally inaccessible passageways or cavities to locate a target object or a particular working area. These tools include endoscopes and laparoscopes used for diagnostic imaging purposes in the medical fields and borescopes as employed in non-medical applications such as inspecting turbine engines or other mechanical devices. These imaging devices typically include a probe having a head portion with an illumination system for illuminating the target object or working area, an imaging system, and a video monitor for viewing an image of the object or area under investigation.

In the medical field, recently developed minimally invasive surgical techniques include endoscopic and laparoscopic examining methods. Endoscopic methods generally encompass visualization of internal body structures by use of an endoscope which is inserted into an orifice or through a previously positioned trocar. Laparoscopy generally refers to visual examination of the interior of the peritoneal cavity by use of a laparoscope introduced into the cavity through the abdominal wall or the vagina. The illumination system of the endoscope or laparoscope typically includes a light box and a fiber optic cable connectable between the scope and the light box. The scope or probe itself also includes fiber optics for transmitting light from the cable to the probe head. In this manner, the scope is manipulated so that an object or area of interest can be positioned adjacent the head and directly illuminated. The imaging system of such scopes or imaging tools may include a charged coupled device (CCD) imager chip positioned in the head of the tool and associated circuitry for receiving an image of the object or area positioned near the head of the probe and transmitting that image to the video monitor. The image processing circuitry converts raw video information received from the imager chip into a monitor ready standard format signal suitable for the particular video monitor. This includes, for example, a standard NTSC, PAL, or Secam color video signal.

Surgeons performing minimally invasive medical operations commonly employ a method of triangulation in association with endoscopic or laparoscopic examining techniques. This method of triangulation involves the use of an endoscope or laparoscope as an imaging tool and at least two other surgical instruments introduced into the surgical site through a body orifice or by use of a trocar. The surgeon observes a displayed image of the target object or working area on the video monitor and performs the desired surgery in a minimally invasive manner by manipulating and operating the surgical instruments deployed in accordance with the techniques of triangulation. During this type of surgical procedure, proper functioning of the scope's illuminating system is critical. In the event the source of illumination in the light box fails, the image on the video monitor will quickly fade to black thus making the surgeon's task impossible. In this situation, the medical procedure must be interrupted and the equipment problem corrected before surgery can resume. This type of illumination source failure is typically encountered when the source lamp simply burns out at the end of its expected life.

OBJECTS AND SUMMARY OF THE INVENTION

It is, therefore, an object of the present invention to improve imaging tools.

Another object of this invention is to extend the operating time of an illumination system used in conjunction with an imaging tool.

It is a further object of the present invention to adapt a bundle of optic fibers to receive direct light from at least two independently activated sources of illumination.

Still another object of the present invention is to avoid the burning out of a source lamp in a light box used in conjunction with an imaging tool, from interrupting a procedure involving reliance on the tool.

An additional object of the present invention is to split a bundle of optic fibers into at least two end segments each positioned to receive direct light from a corresponding independently activated source lamp provided in the light box of an illumination system used in conjunction with an imaging tool.

It is yet a further object of the present invention to allow a surgeon using an endoscope or laparoscope as an imaging tool during a minimally invasive surgical procedure, to continue the procedure when a light box source lamp burns out by simply activating a second source lamp provided in the light box.

Still yet another object of the present invention is to split a bundle of optic fibers into at least two end segments each positioned to receive direct light from a corresponding independently activated source lamp provided in the light box of an illumination system used in conjunction with an imaging tool so that a second lamp may be quickly activated to double the light output at the distal end of the tool.

These and other objects are attained in accordance with the present invention wherein there is provided a light cable for transmitting light from a light source to a distal end of an imaging tool requiring a beam of directed light to illuminate a working area or target object. In accordance with one aspect of this invention, the present light cable is provided with a flexible outer cable member including at least one layer of protective material, a bundle of optic fibers contained within said flexible outer cable member, a first adaptor connected to a first end of the light cable for connecting the first end of the light cable to an imaging tool, and a second adaptor connected to a second end of the light cable for connecting the second end of the light cable to a light box. According to another aspect of this invention, the second adaptor is formed to split the bundle of optic fibers proximate the second end of the light cable into at least two end segments each being directed with a predetermined orientation so that light directed into any one of the at least two end segments is transmitted to the first end of the light cable.

In accordance with further aspects of the present invention, the second adaptor means is provided with a base member secured to the second end of the light cable and a hollow shaft member extending from the base member for insertion into the light box. The hollow shaft member includes a distal end and a proximal end secured to the base member, and is further provided with a head member secured within the distal end of the hollow shaft member. The bundle of optic fibers is extended through the base member and the hollow shaft member, and then directed into the head member which is provided with an exterior bevelled surface for each of the at least two tip segments. Each of the fiber optic end segments terminates with an optically polished surface that is coplanar with its respective bevelled surface on the head member.

According to yet another aspect of this invention, the light box used in conjunction with the present light cable is provided with at least two independent sources of illumination, each having a predetermined orientation to direct light into a corresponding tip segment formed on the second end of the light cable. The at least two light sources are independently wired so that they may be consecutively operated to extend the operating time of the imaging tool. Thus, a procedure involving reliance on the tool does not need to be interrupted when one of the light sources burns out.

BRIEF DESCRIPTION OF THE DRAWING

Further objects of the present invention together with additional features contributing thereto and advantages accruing therefrom will be apparent from the following description of a preferred embodiment of the invention which is shown in the accompanying drawing, wherein.

DETAILED DESCRIPTION OF A PREFERRED EMBODIMENT

Figure 1:
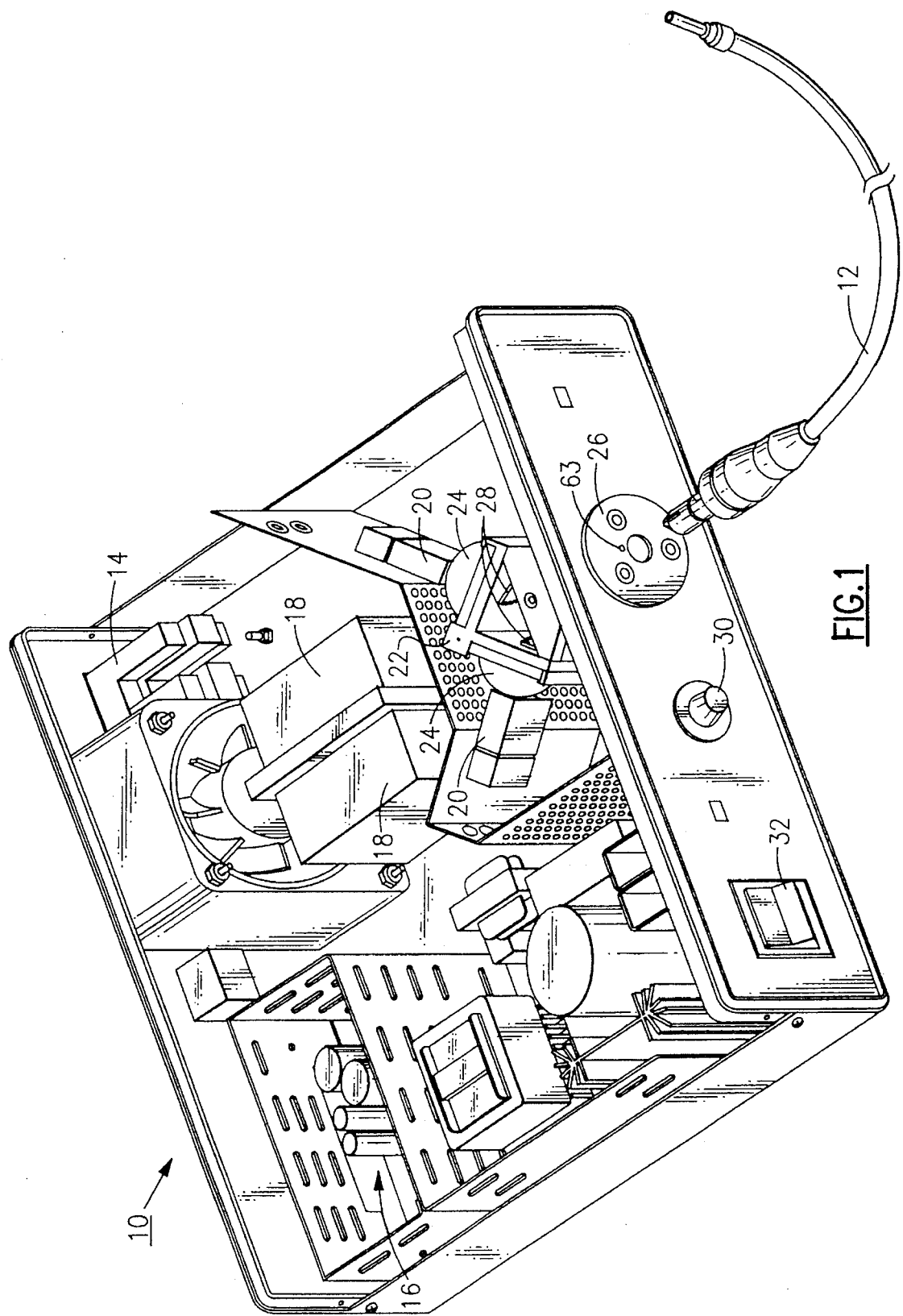
FIG. 1 is a perspective view of a light box and bifurcated fiber cable in accordance with the present invention.

Referring now to FIG. 1, there is shown a light box 10 and a bifurcated light cable 12 in accordance with the present invention. The light box 10 includes a 112 volt AC input which is converted to direct current in a smart switching DC power supply generally referenced 16. Power from the supply 16 is used to power a pair of ballasts 18—18. Each ballast powers and controls a lamp 20 while each of the two lamps 20 is part of a lamp assembly 22. A related type of single ballast and lamp apparatus is fully disclosed in U.S. Pat. No. 5,291,100 entitled "Low Watt Metal Halide Lamp Apparatus" issued to R. J. Wood Mar. 1, 1994 and assigned to the assignee of the present application.

As illustrated in FIG. 1, each of the lamps 20 includes a reflector 24 formed in the shape of a truncated ellipsoid. The reflectors 24 are oriented in the lamp assembly 22 to direct light from the lamps at a right angle relative to each other and generally toward a light port 26. The lamps 20 employed in the light box 10 may be selected from the type of metal halide lamps disclosed in the commonly assigned U.S. Pat. No. 5,083,059 entitled "Electrode For Metal Halide Discharge Lamp" issued to T. W. Graham et al. Jan. 21, 1992. The lamps 20 are preferably such metal halide arc discharge lamps having a power input rating within a range of between about 1.5 watts and 35.0 watts. The intensity of the output of the lamps 20 directed toward the light port 26 is mechanically controlled by a light control vane 28 positioned adjacent each of the lamps. The control vanes 28 are adjusted by an operator by use of a lamp intensity control knob 30 positioned on the front of the light box 10. An on/off toggle switch 32 is provided to switch the light box between an operating condition and a completely shut-down, unpowered condition. A cooling fan 34 is provided to remove heat from the interior of the light box 10 during operation thereof.

Figure 2:
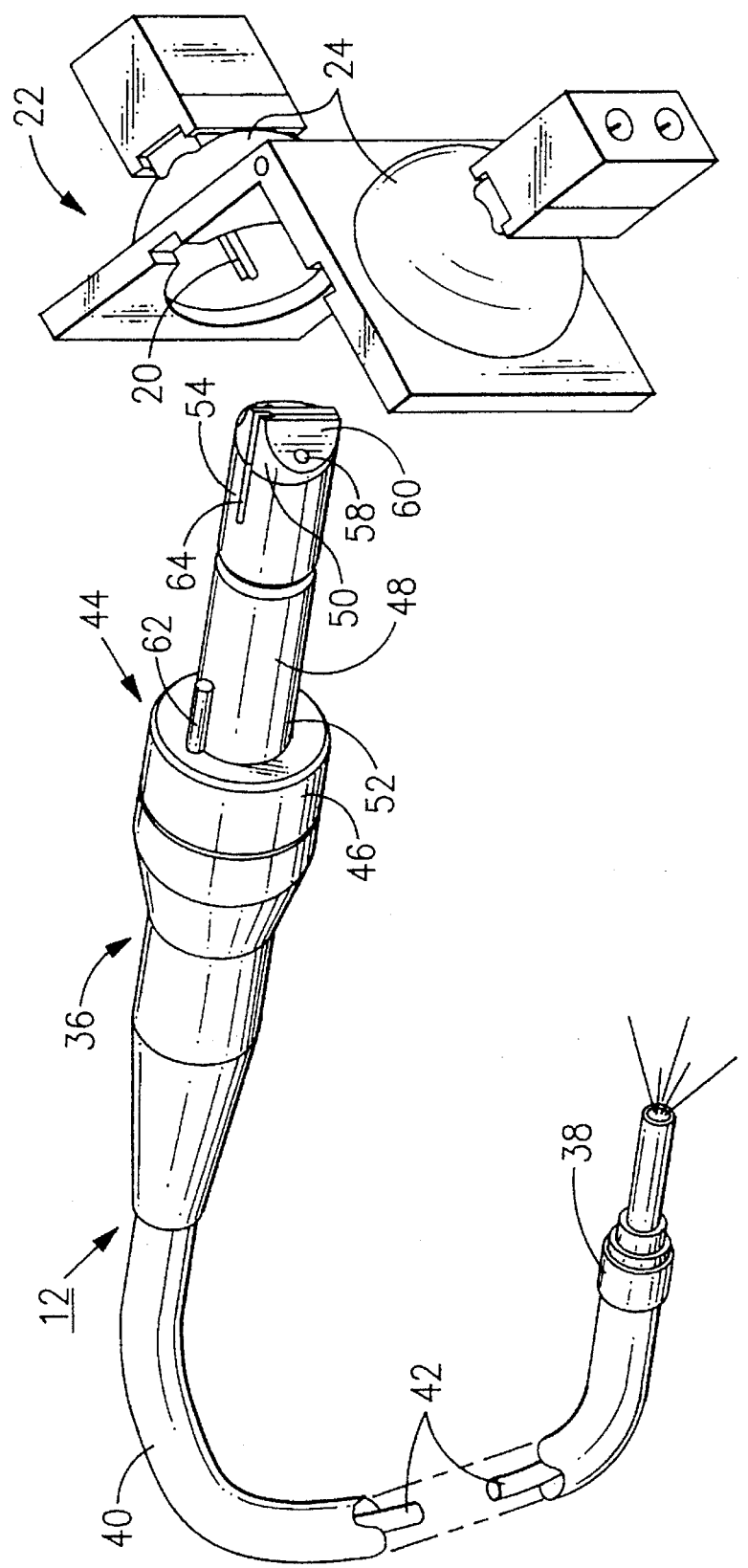
FIG. 2 is an isolated perspective view of the fiber cable illustrated in FIG. 1 shown in conjunction with a dual lamp assembly according to this invention.
Figure 3:
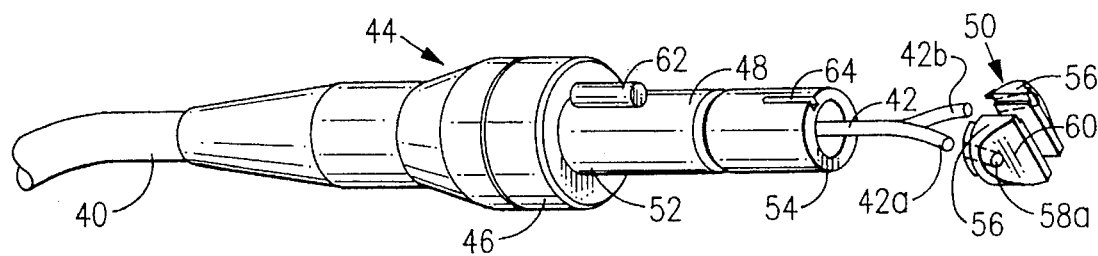
FIG. 3 is an exploded isolated perspective view of the proximal end of the present fiber cable illustrating the fiber end and tip assembly.
Figure 4:
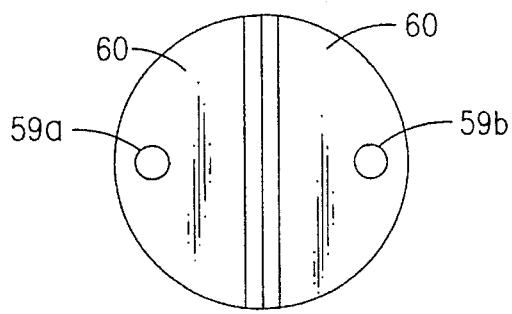
FIG. 4 is an isolated front elevation view of the tip assembly of the present bifurcated optic fiber cable.
Figure 5:
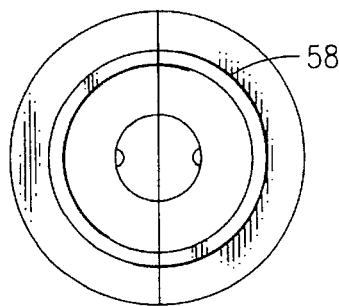
FIG. 5 is an isolated rear elevation view of the tip assembly illustrated in FIG. 4.
Figure 6:
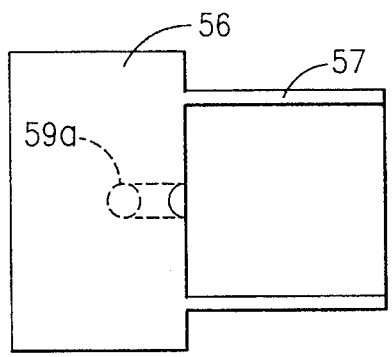
FIG. 6 is a side elevation view of the interior of one of the identical half segments forming the tip assembly of the present invention.
Figure 7:
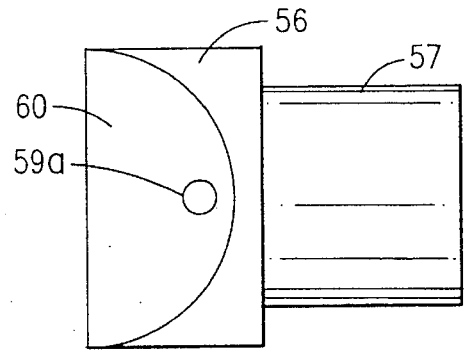
FIG. 7 is a side elevation view of the interior of one of the identical half segments forming the tip assembly of the present invention.

The bifurcated light cable 12 used in conjunction with the above-described light box 10, will now be discussed in detail with particular reference to FIGS. 2 and 3. The light cable 12 includes a proximal end 36, a distal end 38, a mid-section 40, and an internal bundle of optic fibers 42. The mid-section 40 is formed of at least one flexible outer cable covering or sheath which contains substantially the entire length of the fiber optic bundle 42. The distal end 38 of the light cable 12 is adapted to connect into any one of a variety of imaging tools such as video medical endoscopes or industrial borescopes to provide illumination for a target object or area under inspection. The proximal end 36 of the light cable 12 includes an adaptor 44 for securely connecting the light cable 12 into the light port 26 of the light box 10.

The adaptor 44 includes a base member 46, a hollow shaft member 48, and a head member 50. The hollow shaft member 48 includes a proximal end 52 secured to the base member 46, and a distal end 54 into which the head member 50 is secured. As best illustrated in FIG. 3, the head member 50 is comprised of two tip segments 56–56 which split the bundle of optic fibers 42 proximate the distal end 54 of the shaft member 48 into least two fiber bundle end segments 42a and 42b. As shown in FIGS. 4–7, each of the tip segments 56 are preferably identical and include a half-round annulus 57 such than when the two tip segments 56 are assembled together, the two half-round annuluses 57 form a collar 58 which is securely fit into the distal end 54 of the hollow shaft member 48. Each of the bundle end segments 42a and 42b is directed through a corresponding hole 59a and 59b, respectively, with a predetermined orientation so that light from one of the lamps 20 is directed straight into one of the end segments 42a or 42b. Each of the tip segments 56 is provided with a bevelled surface 60 onto which one of the corresponding holes 59a or 59b opens. In the present embodiment, the two bevelled surfaces 60 are oriented ninety (90) degrees to each other.

With reference again to FIGS. 2 and 3, it is shown that the base member 46 is provided with a centering pin 62 corresponding to a receptical aperture 63 (FIG. 1) formed adjacent the light port 26, while the hollow shaft segment 48 is provided with a centering slot or key way 64 which traverses the length of the head member 50. In this manner, the shaft member 48 may be fully inserted into the light port 26 only when the centering pin 62 engages the receptical aperture 63 and a key (not shown) engages the centering slot 64. In this condition, each of the beveled surfaces 60 is positioned parallel to a plane containing the open end of an adjacent reflector 24. The bevelled surfaces 60 and the end of their corresponding bundle end segments 42a and 42b are preferably optically polished to allow maximum light transmission into the fiber bundle 42.

The light box 10 and light cable 12 may be employed to illuminate an imaging tool such as a video endoscope during a medical diagnosis or surgical operation. During such a procedure, only one of the two lamps is illuminated. Thus one of the advantages of the present invention is that in the event the operating lamp burns out, the second lamp may be quickly illuminated so that the image provided by the endoscope can be maintained without having to change a lamp and interrupt the surgery. An additional advantage of the present light box and cable assembly is acheived by providing the light box 10 with circuitry allowing both lamps 20 to operate simultaniously. In this manner, when a respective imaging tool is operating with one lamp 20 illuminated, the second lamp 20 may be activated on demand to effectively double the light intensity output directed at the proximal end 36, and thus the distal end 38, of the cable 12.

While this invention has been described in detail with reference to a certain preferred embodiment, it should be appreciated that the present invention is not limited to that precise embodiment. For example, more than two fiber ends and/or corresponding lamps may be employed. In addition, it is currently contemplated that the switching between the lamps may be done either manually or electrically by use of control circuitry incorporated in the light box. Furthermore, it would readily be appearent to one skilled in the art to employ light vanes, apperture wheels, or electronic circuitry to variably control the output light intensity of one or both of the lamps. Thus, in view of the present disclosure which describes the current best mode for practicing the invention, many modifications and variations would present themselves to those of skill in the art without departing from the scope and spirit of this invention, as defined in the following claims.

What is claimed is:

1. A light cable for transmitting light from a light source to a distal end of an imaging tool requiring a beam of directed light to illuminate a working area or target object, said light cable comprising:

a flexible outer cable member including at least one layer of protective material;

a bundle of optic fibers contained within said flexible outer cable member;

first adaptor means, connected to a first end of the light cable, for securely connecting said first end of the light cable to a respective imaging tool; and second adaptor means, connected to a second end of the light cable, for securely connecting said second end of the light cable to a light box including at least two sources of illumination, wherein said bundle of optic fibers is split, at a light receiving end of said bundle proximate to said second end of the light cable, into at least two end segments, such that light from each one of said at least two sources of illumination directed into a respective one of said at least two end segments at said light receiving end of said bundle is transmitted to a same light emitting end of said bundle proximate to said first end of the light cable, and wherein said second adaptor means includes:

a base member secured to said second end of the light cable;

a hollow shaft member extending from said base member, said hollow shaft member having a distal end and a proximal end secured to said base member; and a head member secured within the distal end of said hollow shaft member, said bundle of optic fibers extending through said base member and said hollow shaft member, and into said head member which is provided with an exterior head surface for each of said at least two end segments, each of said end segments terminating with an end surface being substantially coplanar with its respective head surface.

2. The light cable according to claim 1 wherein said head surface for each of said at least two end segments is a bevelled planar surface formed on said head member.

3. The light cable according to claim 2 wherein said two bevelled surfaces are oriented 90 degrees relative to each other.

4. The light cable according to claim 1 wherein each of the end surfaces of each of said at least two end segments is optically polished.

5. The light cable according to claim 1 wherein said second adaptor means comprises means for detachably connecting said second end of the light cable to said light box.

6. The light cable according to claim 5 wherein said head member includes two identical half segments which when assembled together form a collar insertable into the distal end of said hollow shaft member, and a substantially solid tip including two bevelled surfaces each corresponding to one of the two end segments formed in said second end of the light cable, said collar being formed on one end of the solid tip and said two bevelled surfaces being formed on another end of the solid tip.

7. The light cable according to claim 6 wherein each half segment of said head member includes one of said two bevelled surfaces, and a bore hole extending from proximate said collar, through said substantially solid tip, and opening onto a respective head surface, each bore hole for receiving one of the two optic fiber end segments and directing the fiber end segment towards its respective head surface.

8. A light cable assembly for transmitting light from a light source to a distal end of an imaging tool requiring a beam of directed light to illuminate a working area or target object, said light cable assembly comprising:

a flexible outer cable member including at least one layer of protective material;

a bundle of optic fibers contained within said flexible outer cable member;

first adaptor means connected to a first end of the light cable, said first adaptor means for securely connecting said first end of the light cable to a respective imaging tool;

a light box containing at least two independent sources of illumination each having a predetermined orientation relative to said light box; and second adaptor means connected to a second end of the light cable, said second adaptor means for securely connecting said second end of the light cable to said light box, and for splitting said bundle of optic fibers at a light receiving end of said bundle proximate to said second end of the light cable into at least two end segments each directed with a predetermined orientation being optically aligned with a corresponding source of illumination within said light box, said second adaptor means including a head member provided with an exterior head surface for each of said at least two end segments, and each of said end segments terminating with an end surface being substantially coplanar with its respective head surface, whereby said at least two sources of illumination may be consecutively operated to extend uninterrupted illumination of the working area or target object under investigation.

9. The light cable assembly according to claim 8 wherein said second adaptor means includes:

a base member secured to said second end of the light cable; and a hollow shaft member extending from said base member, said hollow shaft member having a distal end and a proximal end secured to said base member, and wherein said head member is secured within the distal end of said hollow shaft member, said bundle of optic fibers extending through said base member and said hollow shaft member, and into said head member which is provided with an exterior head surface for each of said at least two end segments, each of said end segments terminating with an end surface being substantially coplanar with its respective head surface, each of said respective head surfaces being positioned within the light box substantially perpendicular to directed electromagnetic flux produced by a corresponding one of said at least two independent sources of illumination.

10. The light cable assembly according to claim 9 wherein said head surface for each of said at least two end segments is a bevelled planar surface formed on said head member.

11. The light cable assembly according to claim 9 wherein each of the end surfaces of each of said at least two end segments is optically polished.

12. The light cable assembly according to claim 9 wherein said bundle of optic fibers proximate said second end of the light cable is split into two end segments and said light box includes two independent sources of illumination each being a metal halide arc discharge lamp having a power input rating within a range of between about 1.5 watts and 35.0 watts.

13. The light cable assembly according to claim 12 wherein said head member includes two identical half segments which when assembled together form a collar insertable into the distal end of said hollow shaft member, and a substantially solid tip including two bevelled surfaces each corresponding to one of the two end segments formed in said second end of the light cable, said collar being formed on one end of the solid tip and said two bevelled surfaces being formed on another end of the solid tip.

14. The light cable assembly according to claim 13 wherein each half segment of said head member includes one of said two bevelled surfaces, and a bore hole extending from proximate said collar, through said substantially solid tip, and opening onto a respective bevelled surface, each bore hole for receiving one of the two optic fiber end segments and directing the fiber end segment towards its respective bevelled surface.

15. The light cable assembly according to claim 13 wherein said two bevelled surfaces are oriented 90 degrees relative to each other.

16. The light cable assembly according to claim 13 wherein each metal halide arc discharge lamp is positioned within an ellipsoid reflector for directing electromagnetic flux from the lamp perpendicularly toward said respective bevelled surface and corresponding fiber optic end surface.

17. The light cable assembly according to claim 8 wherein said at least two sources of illumination may be simutaniously operated to provide increaded illumination of the working area or target object under investigation.

\* \* \* \* \*